(12) United States Patent
Wolf et al.

(10) Patent No.: US 11,369,723 B2
(45) Date of Patent: Jun. 28, 2022

(54) PERITONEAL DIALYSIS MACHINE

(71) Applicant: Fresenius Medical Care Deutschland GmbH, Bad Homburg (DE)

(72) Inventors: Klaus Wolf, Muedesheim (DE); Peter Wabel, Darmstadt (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 230 days.

(21) Appl. No.: 16/613,437

(22) PCT Filed: May 16, 2018

(86) PCT No.: PCT/EP2018/062816
§ 371 (c)(1),
(2) Date: Nov. 14, 2019

(87) PCT Pub. No.: WO2018/210973
PCT Pub. Date: Nov. 22, 2018

(65) Prior Publication Data
US 2020/0164130 A1    May 28, 2020

(30) Foreign Application Priority Data
May 16, 2017   (DE) ..................... 10 2017 110 607.3

(51) Int. Cl.
*A61M 1/28*    (2006.01)
(52) U.S. Cl.
CPC ........... *A61M 1/28* (2013.01); *A61M 2205/18* (2013.01); *A61M 2205/3334* (2013.01)
(58) Field of Classification Search
CPC ........ A61M 1/28; A61M 1/281; A61M 1/282; A61M 2205/18; A61M 2205/3334; A61M 2205/70; A61M 1/1601; A61M 1/1615; A61M 1/284; A61M 2205/3331; A61M 2205/3379; A61M 2205/3389; A61M 2205/3396; A61M 2205/50; A61M 2210/1017; A61M 2210/10
See application file for complete search history.

(56) References Cited

U.S. PATENT DOCUMENTS

2009/0012455 A1    1/2009  Childers et al.
2015/0005699 A1 *  1/2015  Burbank ................ A61M 1/28
                                                          604/29

FOREIGN PATENT DOCUMENTS

WO   WO-2007114447 A1 * 10/2007   ........ A61M 5/14546
WO   WO 2013/141896       9/2013

* cited by examiner

*Primary Examiner* — Amber R Stiles
*Assistant Examiner* — Avery Smale
(74) *Attorney, Agent, or Firm* — Jacobson Holman PLLC

(57) ABSTRACT

A peritoneal dialysis machine carries out of a peritoneal dialysis treatment having recurring cycles, the recurring cycles involving an inflow phase, a dwell period and a drainage phase for a dialysis fluid, wherein the peritoneal dialysis machine has a control unit and a measurement apparatus for determining the inflow rate and/or drainage rate of the dialysis fluid to and from a patient, wherein the control unit is configured to carry out a comparison between a time progression curve of the inflow rate and/or of the drainage rate determined by the measurement apparatus during the inflow phase and/or the drainage phase and a corresponding reference curve and to recognize on the basis of the comparison a disturbance in inflow and/or drainage of the dialysis fluid to and from the patient.

10 Claims, 4 Drawing Sheets

PERITONEAL DIALYSIS MACHINE

CROSS-REFERENCE TO RELATED APPLICATIONS

This application is a U.S. national stage application under 35 USC 371 of International Patent Application No. PCT/EP2018/062816, filed May 16, 2018, which claims priority to German Patent Application No. DE10 2017 110 607.3, filed May 16, 2017, the entire contents of each of which are incorporated herein by reference.

The invention relates to a machine for the carrying out of a peritoneal dialysis treatment on a patient.

Peritoneal dialysis is also abbreviated to PD. There are various PD processes, including the processes of automated peritoneal dialysis (APD) carried out using peritoneal dialysis machines. In ADP all the treatment steps or at least some of the treatment steps are carried out in an automated manner. Said steps can, for example, be the switching on or off of pumps, the opening or closing of valves, etc.

The effecting of a flow of dialysis solution can take place gravimetrically, i.e. due to gravity, and/or by means of one or more pumps.

The present invention is not restricted to a specific kind of PD, i.e. it comprises automatic machines, non-automatic machines, gravimetric machines and also machines working with pumps.

In PD, the machine conducts a dialysis solution to the patient, into the abdominal cavity, for example, in an automated manner via a catheter by means of a pump or gravimetrically in an inflow phase.

The dialysis solution is then left in the abdominal cavity during a dwell period. In this process, low-molecular substances can pass from the blood via the capillary vessels of the peritoneum into the dialysis solution since a concentration gradient is present. Water can furthermore be removed from the body in this manner provided that the dialysis solution has a higher content of osmotically active substances than the blood. After the end of the dwell period, the machine removes the dialysis solution enriched with eliminated substances and consequently used up in a drainage phase from the abdominal cavity again via the catheter. The fluid exchange can take place gravimetrically or actively by means of a pump.

The cycle of inflow phase, dwell period and drainage phase is repeated several times in typical process management routines, for example over night while the patient is asleep. A new introduction phase is always started whenever the machine determines that the drainage phase has ended, i.e. that the used dialysis fluid has been completely or partially drained from the abdominal cavity of the patient.

Currently known peritoneal dialysis machines make the determination whether a drainage phase has ended and a new inflow phase can begin purely with reference to criteria that are normally adopted at the end of the drainage phase, that is e.g. a reached minimum drainage volume and a falling below of a specific flow rate. It can occur in this respect that disturbances in the drainage, that result, for example, from an unintentional kinking of the drainage hose, are not recognized and that the drainage phase is thus aborted prematurely and the subsequent inflow phase starts too soon. It is, however, desirable in the interest of a treatment that is as efficient as possible that the consumed dialysis solution is removed as completely as possible from the abdominal cavity in every drainage phase to ensure exchange volumes that are as large as possible.

It is the object of the invention to provide a peritoneal dialysis machine by which the progress of the drainage or the actual end of the drainage phase can be recognized more reliably.

Against this background, the invention relates to a peritoneal dialysis machine for the carrying out of an automated peritoneal dialysis treatment having recurring cycles, the cycles comprising an inflow phase, a dwell period and a drainage phase for the dialysis fluid, wherein the machine has a control unit and a measurement apparatus for determining the inflow and/or drainage rate of the dialysis fluid to and from a patient. Provision is made in accordance with the invention that the control unit is configured to carry out a comparison between a time progression curve of the inflow rate and/or of the drainage rate determined by the measurement apparatus during an inflow phase and/or a drainage phase and a corresponding reference curve and to recognize on the basis of this comparison a disturbance in the inflow and/or drainage of the dialysis fluid to and from the patient.

The machine is preferably configured such that the inflow and the drainage take place in an automated manner by means of a control unit of the machine.

Provision can be made that a reference curve for the time progression of the drainage rate during the inflow phase and/or the drainage phase is stored in the control unit and that a measurement comparison curve can be compared with it. An atypical time progression of the inflow rate and/or of the drainage rate can be recognized with reference to the comparison and can indicate a disturbance in the inflow phase or in the drainage phase. The recognition accuracy as to whether the total or desired quantity of dialysis fluid has actually been drained from the patient can, for example, be improved on this basis. Counter-measures can furthermore be initiated in the event of a disturbance.

Figure 1:
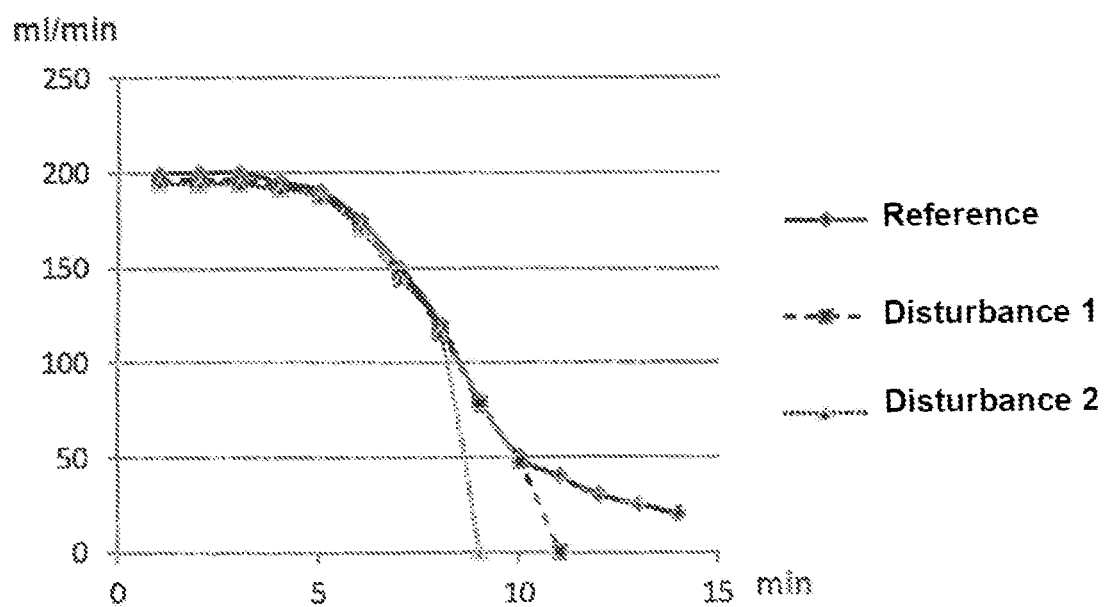
FIG. 1 graphically depicts the possible time progressions of the drainage rate (volume/time) in the abdominal cavity of a patient during the drainage phase with gravimetric, i.e. passive, drainage of a dialysis treatment.

The present invention preferably relates to actively conveying APD machines, i.e. peritoneal dialysis machines in which the inflow and/or the drainage of the dialysis solution into/from the patient take(s) place by means of one or more pumps and also peritoneal dialysis machines which work gravimetrically and in which the named inflow and/or drainage take(s) place by means gravity and without pumps. The control of the fluid flows in both cases preferably takes place in an automated manner, e.g. by opening and closing valves, etc.

Provision is made in an embodiment that the control unit is configured such that, on a recognition of a disturbance in the drainage of the dialysis fluid from the patient, a time-limited observation phase is started during which the drainage rate is measured and a check is made with respect to the re-reaching of a minimal flow. This embodiment is therefore a wait and see approach whether a minimal flow is again adopted, for example because a kink in the catheter or in the hose releases on its own due to a movement of the patient. Further measures can be provided if the desired minimal flow is not reached again during the observation phase, that can, for example, last between 1 and 5 minutes. The minimal flow can, for example, correspond to that flow that would be provided in the reference curve at a specific time of the drainage phase, corrected as required by a tolerance deduction.

Provision is made in an embodiment that the control unit is configured such that, on a recognition of a disturbance in the drainage of the dialysis fluid from the patient, a volume is conveyed in the direction of the patient. The quality of the line can be checked using this measure. The conveying can, for example, take place actively by means of a fluid pump. The measure can optionally be taken after the elapse of an observation phase if such a phase is provided.

Provision is made in an embodiment that the control unit is configured such that a signal is output on a recognition of a disturbance in the inflow and/or drainage of the dialysis fluid to or from the patient.

Provision can be made for this purpose that the machine has a signal unit or an interface for communication with an external signal unit. The signal output can represent an attempt to improve the situation. The signal can, for example, serve to wake up or stimulate the patient or to draw his attention to the fact that he should move or should actively set the catheter into operation again. Suitable signals, for example, comprise visual signals, audio signals or vibration signals. The measure can optionally be taken after the elapse of an observation phase and/or after conveying a volume in the direction of the patient if such measures are provided.

Provision is made in an embodiment that the control unit is configured such that an optimization of the machine configuration can be carried out on the basis of the comparison. For example, criteria as to when a drainage phase is to be considered ended can be adapted to a patient in accordance with the reference curve and the measured curve.

Provision is made in an embodiment that the reference curve is a patient-independent function that is stored in the control unit. The reference curve can, for example, be fixed schematically using prescription parameters such as the quantity of fluid administered.

Provision is made in an embodiment that the reference curve is a patient-individual function. Provision can, for example, be made that a reference curve is recorded in a setting cycle prior to the start of treatment. Provision can furthermore be made, for example, that the reference curve is determined from a plurality of measured curves by e.g. forming a mean. The reference curve can be formed by a superposition of curves that were measured in a specific number of preceding cycles or treatments; it can therefore be a patient-individual mean value.

Figure 3:
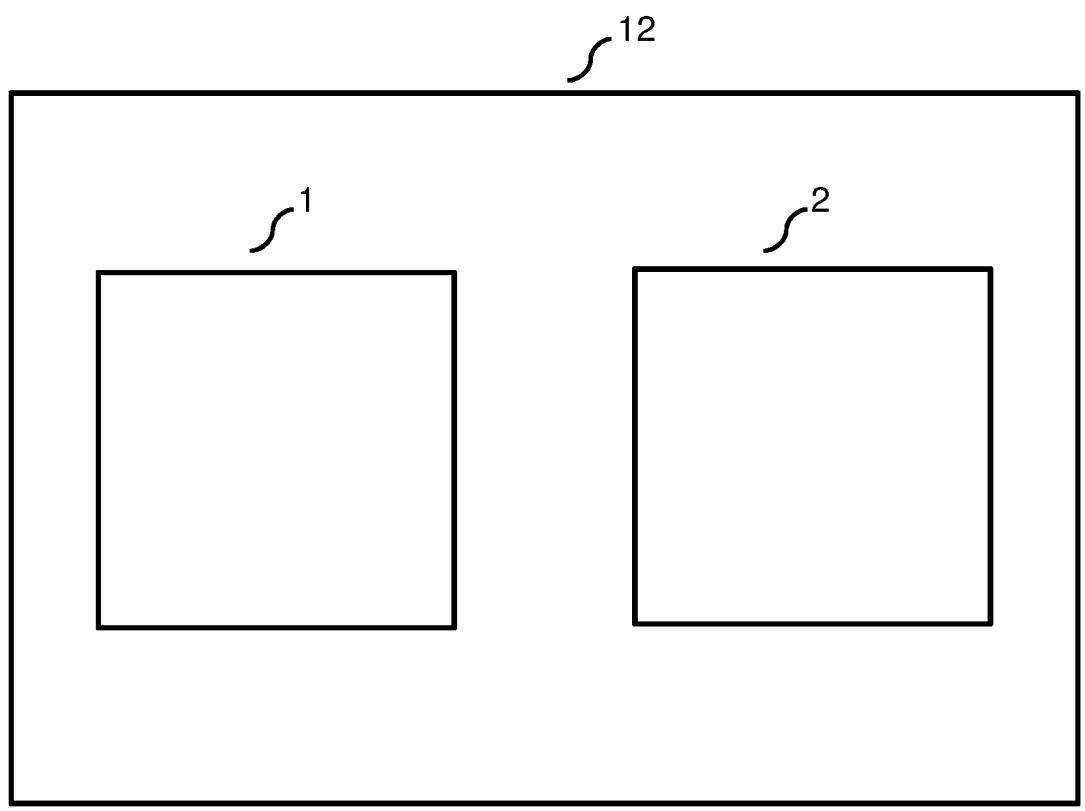
FIG. 3 schematically represents the peritoneal dialysis machine as a gravimetrically working machine in accordance with the present invention.

Provision is made in an embodiment that the peritoneal dialysis machine is a gravimetrically working machine 12 comprising control unit 1 and measurement apparatus 2 as shown in FIG. 3. One or more valves can be provided, for example, and the control unit 1 can be configured such that the or a valve is opened after the dwell phase and before the start of the drainage phase to enable a gravimetric drainage of dialysis fluid from the patient and/or such that the or a valve is opened after the drainage phase and before the start of the inflow phase to enable a gravimetric inflow of dialysis fluid to the patient.

Figure 4:
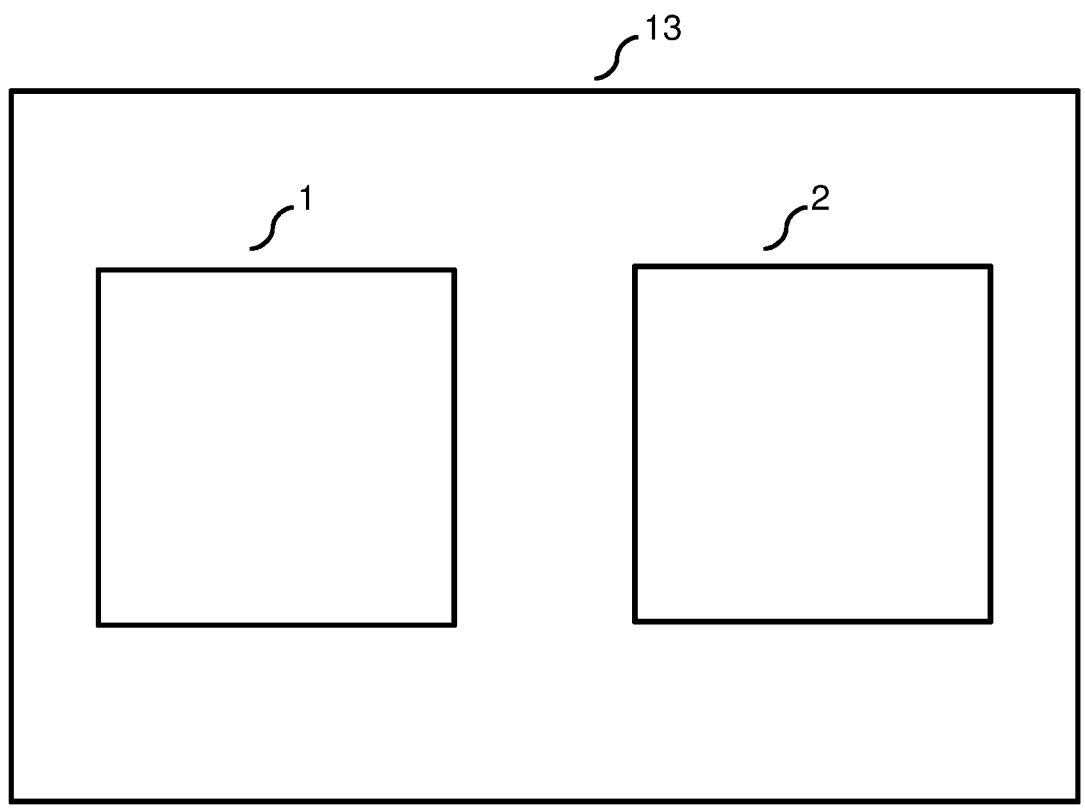
FIG. 4 schematically represents the peritoneal dialysis machine as an actively conveying machine in accordance with the present invention.

Provision is made in an embodiment that the peritoneal dialysis machine is an actively conveying machine 13 comprising control unit 1 and measurement apparatus 2 as shown in FIG. 4. One or more pumps can, for example, be provided and the control unit can thus be configured to withdraw dialysis fluid from the patient during the drainage phase using the or a pump and/or to supply dialysis fluid to the patient during the inflow phase using the or a pump.

The invention furthermore comprises a method of carrying out a peritoneal dialysis using a peritoneal dialysis machine in accordance with the invention, wherein a comparison is carried out between a measured time progression curve of the inflow rate and/or of the drainage rate during an inflow and/or drainage phase and a corresponding reference curve, and wherein a disturbance in the inflow and/or drainage of the dialysis fluid to or from the patient is recognized on the basis of this comparison. Advantageous embodiments of the method result from the above description of the configuration of the control unit in the peritoneal dialysis machine in accordance with the invention.

Further details and advantages of the invention result from the following embodiment described with reference to the FIG. 1. FIG. 1 shows possible time progressions of the drainage rate (volume/time) in the abdominal cavity during the drainage phase with gravimetric, i.e. passive, drainage.

Figure 2:
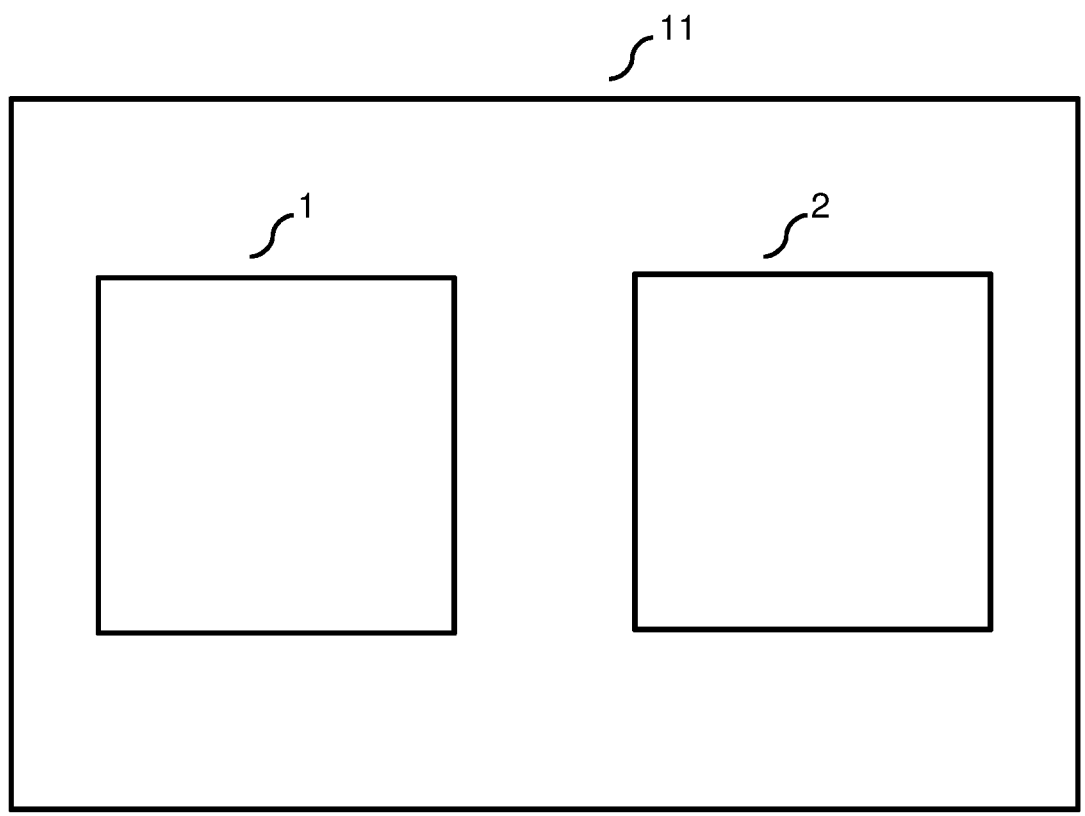
FIG. 2 schematically represents a peritoneal dialysis machine in accordance with the present invention.

In accordance with the embodiment, a peritoneal dialysis machine 11 is provided as shown in FIG. 2 that is intended for the carrying out of an automated peritoneal dialysis treatment having recurring cycles comprising an inflow phase, a dwell period, and a drainage phase for the dialysis fluid. The machine comprises a control unit 1 and a measurement apparatus 2 for determining the inflow rate and/or the drainage rate of the dialysis fluid to or from a patient. It furthermore comprises a dialyzate pump for conveying dialysis fluid to the patient as well as a drainage valve that is opened by the control unit after the dwell phase and before the start of the drainage phase to enable a gravimetric drainage of dialysis fluid from the patient.

A reference curve for the time progression of the drainage phase is stored in memory, e.g. in the control unit, that is patient-individual and that is formed by a superposition of curves that were measured in the course of drainage procedures in a specific number of preceding cycles. An algorithm is furthermore stored on the control unit with reference to which a comparison can be carried out between a time progression curve of the drainage rate determined by the measurement apparatus during a further drainage phase and the reference curve. The algorithm furthermore permits a disturbance in the drainage of the dialysis fluid from the patient to be recognized on the basis of this comparison.

Instead of a memory that is physically located in the machine, the memory can also be located on a movable articles such as on a patient card or on any other data store that does not form part of the machine.

If a disturbance is recognized, the control unit is configured to take a series of measures.

A specific observation phase, for example a three-minute observation phase, is first started in which the drainage rate is continuously measured and in which a check for the re-reaching of the minimal flow is checked. The minimal flow corresponds to that flow that should be present before the occurrence of the disturbance, less a specific tolerance interval, for example 30%.

If the minimal flow is not re-reached in the course of the observation phase, the control unit starts the dialyzate pump to convey a specific, smaller, volume of, for example, 100 ml in the direction of the patient. The quality of the line can be checked using this measure.

The aforesaid numerical values are examples that do not restrict the invention.

Alternatively or additionally, a warning signal, preferably a piece of acoustic information, can be output.

If a disturbance results as part of this filling test that could, for example, indicate a kink in the catheter, the control unit outputs an acoustic signal to the signal unit installed in the machine. It should be suitable to wake up the patient and to alert him to change his position.

After this step, a reevaluation takes place in the form of a repeat observation phase and a repeat filling test. The signaling can also be repeated in the same form or in a more intensive form such that the patient then actually gets up as necessary to check the function of the lines.

The "Reference" curve of the FIGURE shows a time progression of the drainage rate in a machine in accordance with the embodiment in the normal case. The drainage rate drops due to the increasing emptying of the patient due to the reducing hydrostatic pressure. This time duration can amount to 5 min for example.

The curve "Disturbance 1" of the FIGURE shows a time progression of the drainage rate for the event that the drainage is disturbed just before the end of the drainage phase. This case can occur, for example, if the drainage catheter sags or is otherwise clogged or jammed/kinked so that the further drainage no longer continues when a specific hydrostatic pressure is fallen below.

The curve "Disturbance 2" of the FIGURES finally shows a time progression of the drainage rate for the case that the outflow is already disturbed a little earlier. This case can, for example, occur if the drainage catheter is kinked or otherwise blocked, e.g. clogged, by a movement of the patient while asleep such that the further drainage no longer continues when a specific hydrostatic pressure is fallen below.

Advantages of the solution in accordance with the invention comprise, for example, avoiding an early switchover from a drainage phase into the inflow phase of the following cycle as well as an improvement of the drainage behavior overall and thus an optimization of the therapy. The number of drainage phases ended in an unauthorized or unwanted manner can be reduced. There are also fewer possibilities that the user negatively influences the machine behavior. The patient has improved feedback, for example with regard to his sleeping position, the height of the bed or the installation site of the machine.

The invention claimed is:

1. A peritoneal dialysis machine for carrying out of a peritoneal dialysis treatment having recurring cycles, the recurring cycles comprising an inflow phase, a dwell period and a drainage phase for a dialysis fluid, wherein the peritoneal dialysis machine has a control unit and a measurement apparatus for determining the inflow rate (volume/time) and/or drainage rate (volume/time) of the dialysis fluid to and from a patient, characterized in that
the control unit is configured to carry out a comparison between a time progression curve of the inflow rate and/or of the drainage rate determined by the measurement apparatus during the inflow phase and/or the drainage phase and a corresponding reference curve and to recognize on a basis of the comparison a disturbance in inflow and/or drainage of the dialysis fluid to and from the patient.

2. The peritoneal dialysis machine in accordance with claim 1, characterized in that the control unit is configured such that, on the recognition of the disturbance in the drainage of the dialysis fluid from the patient and/or on a recognition of a disturbance in the inflow of the dialysis fluid to the patient, a time-limited observation phase is started during which the drainage rate or the inflow rate is measured and a check is made with respect to a re-reaching of a flow or of a minimal flow.

3. The peritoneal dialysis machine in accordance with claim 1, characterized in that the control unit is configured such that, on the recognition of the disturbance in the drainage of the dialysis fluid from the patient, a volume is conveyed in a direction of the patient.

4. The peritoneal dialysis machine in accordance with claim 1, characterized in that the control unit is configured such that a signal is output on the recognition of the disturbance in the inflow and/or the drainage of the dialysis fluid to or from the patient.

5. The peritoneal dialysis machine in accordance with claim 4, characterized in that the signal is a visual signal, an acoustic signal or a vibration signal.

6. The peritoneal dialysis machine in accordance with claim 1, characterized in that the control unit is configured such that an optimization of the machine configuration is carried out on the basis of the comparison.

7. The peritoneal dialysis machine in accordance with claim 1, characterized in that the corresponding reference curve is a patient-independent function that is stored in the control unit.

8. The peritoneal dialysis machine in accordance with claim 1, characterized in that the corresponding reference curve is a patient-individual function.

9. The peritoneal dialysis machine in accordance with claim 1, characterized in that the peritoneal dialysis machine is a gravimetrically working machine.

10. The peritoneal dialysis machine in accordance with claim 1, characterized in that the peritoneal dialysis machine is an actively conveying machine.

* * * * *